United States Patent [19]

Mathur

[11] Patent Number: 5,144,046

[45] Date of Patent: Sep. 1, 1992

[54] SYNTHESIS OF CYCLIC KETENE ACETALS

[76] Inventor: Saughagya C. Mathur, 1007 Deer Park Ct., Longview, Tex. 76504

[21] Appl. No.: 654,994

[22] Filed: Feb. 14, 1991

[51] Int. Cl.$^5$ ............... C07D 321/06; C07D 323/02; C07D 323/04
[52] U.S. Cl. ............................ 549/347; 549/376; 549/430
[58] Field of Search ............... 549/430, 347, 376

[56] References Cited

U.S. PATENT DOCUMENTS

| 3,431,281 | 3/1969 | Sawaya | 549/430 |
| 4,559,355 | 12/1985 | Kraatz et al. | 549/347 |
| 4,761,489 | 8/1988 | Gramlich et al. | 549/347 |

FOREIGN PATENT DOCUMENTS

| 95182 | 5/1983 | European Pat. Off. | |
| 1543389 | 9/1969 | Fed. Rep. of Germany | 549/430 |
| 3603661 | 8/1987 | Fed. Rep. of Germany | 549/347 |
| 0154575 | 9/1983 | Japan | 549/347 |
| 1200319 | 7/1970 | United Kingdom | 549/430 |
| 1242785 | 8/1971 | United Kingdom | 549/430 |

OTHER PUBLICATIONS

Bailey et al, *Makromol. Chem., Macromol. Symp.*, vol. 6, 81–100 (1986).
McElvain, S. M. and Curry, J. M.; *Journal American Chemical Society*, vol. 70, 3781–3786 (1948).
Taskinen and Pentikainen, *Tetrahedron*, vol. 34, 2365–2370 (1978).
Bailey et al, *J. Polymer Science* (Poly. Chem. Ed. vol. 20, 3021–3030 (1982).
Fukuda et al, *Tetrahedron Letters*, vol. 27, No. 14, 1587–1590 (1986).

*Primary Examiner*—C. Warren Ivy
*Assistant Examiner*—Amelia A. Owens
*Attorney, Agent, or Firm*—Mark A. Montgomery; William P. Heath, Jr.

[57] ABSTRACT

An improved process for the preparation of cyclic ketene acetals such as 2-methylene-1,3-dioxepane is provided. This process entails reacting at an elevated temperature a halogenated cyclic ketene acetal such as 2-chloromethyl-1,3-dioxepane with a hydroxide compound such as potassium hydroxide in a non-reactive alcohol such as 2-butanol.

12 Claims, No Drawings

SYNTHESIS OF CYCLIC KETENE ACETALS

FIELD OF THE INVENTION

The present invention relates to a process for preparing cyclic ketene acetals. More particularly, the present invention relates to a process for preparing cyclic ketene acetals in stable form, such as 2-methylene-1,3-dioxepane at high yield and conversion.

BACKGROUND OF THE INVENTION

Synthetic polymeric materials are widely used in a variety of applications. The environmental degradability of these polymeric materials has recently become important, primarily due to the concerns of limited landfill space and accumulation of liter. Synthetic polymers are in general not biodegradable. The carbon to carbon bonds in the backbone of most synthetic addition polymers are not very susceptible to biological cleavage and this makes these polymers generally quite resistant to birdegradation.

One possible method of solving this problem would be to blend degradable materials, such as starch, with synthetic polymers so that the structure, such as a film, is broken down and looses its structural integrity by the action of living organisms or light. However, when this happens, the actual synthetic polymer itself is not degraded but is simply in the environment in a particulate form. Thus, synthetic polymers that are themselves biodegradable and would disappear from the environment would be very desirable.

Low melting, low molecular weight polyesters are known to be biodegradable. Synthetic addition polymers with an easily hydrolyzable group, such as an ester group, in the polymer chain are also known to be biodegradable. Copolymers of cyclic ketene acetals such as 2 methylene 1,3 dioxepane and ethylene are known see Bailey et. al., *Makromol. Chem. Macromol Symp., Vol. 6*, 81-100 (1986). These copolymers are prepared with ethylene in the presence of a peroxide initiator resulting in a copolymer containing ester groups in the backbone. Processes for producing these cyclic ketene acetals are known, however, these processes have low yield, low conversion, are time consuming and/or are expensive and in some instances produce unstable cyclic ketene acetals that decompose or polymerize spontaneously.

McElavin, S. M. and Curry, J. M.; *Journal American Chemical Society, Vol.* 70,3781-3786(1948) disclose the synthesis of 2-methylene 1,3-dioxolanes and 1,3-dioxanes by dehydrohalogenation of the corresponding halogenated cyclic acetals using potassium t butoxide in t butyl alcohol. The cyclic ketene acetals were obtained pure only with difficulty because the purer the acetal the more rapidly it polymerized.

U.S. Pat. No. 3,431,281 discloses 2-methylene 1,3-dioxolane which does not immediately polymerize. This compound is prepared by mixing 2-chloromethyl 1,3-dioxolane with a solution of liquid ammonia and a alkali metal such as sodium or potassium. It was disclosed that the monomer could be stored for at least 10 days.

Taskinen and Pentikainen, Tetrahedron, Vol. 34, 2365-2370 (1978) disclose the preparation of 2 methylene 1,3-dioxepane and other cyclic ketene acetals by dehydrohalogenation of the chlorine derivatives with solid potassium t butoxide.

Bailey et. al., *J. Polymer Science (Poly. Chem. Ed. Vol.* 20, 3021-3030(1982) disclose synthesis of 2-methylene-1,3-dioxepane by dehydrohalogenation of the corresponding chlorine derivative using potassium t-butoxide in t butyl alcohol. 2-methylene 1,3-dioxepane can also be prepared using potassium hydroxide in 1-hexadecene with 2-chloromethyl 1,3-dioxepane.

EP 095,182 discloses the synthesis of several cyclic ketene acetals including 2-methylene 1,3-dioxepane using dehydrohalogenation of the halogen derivatives using potassium t butoxide in t butyl alcohol.

Fukuda et. al., Tetrahedron Letters Vol. 27. No. 14, 1587-1590(1986) disclose the synthesis of cyclic ketene acetals using dehydrohalogenation of the chloro derivative by potassium t butoxide in t butyl alcohol.

Although the preparation of cyclic ketene acetals such as 2-methylene-1,3-dioxepane are known the above processes either produce unstable forms, are very slow and expensive, or have poor conversion and selectivity. It would, therefore, be desirable to be able to produce cyclic ketene acetals for the preparation of biodegradable synthetic polymers that are efficient and effective.

SUMMARY OF THE INVENTION

The method for producing cyclic ketene acetals according to the present invention comprises reacting at an elevated temperature a halogenated cyclic ketene acetal with a hydroxide compound selected from alkali metal hydroxides, alkaline earth metal hydroxides, and mixtures thereof in a non reactive alcohol capable of dissolving the hydroxide compound at the elevated temperature, the concentration of the hydroxide compound in the alcohol solution is between about 20 and 80 weight percent based on the total of hydroxide compound and alcohol, thereby producing a cyclic ketene acetal.

DETAILED DESCRIPTION OF THE INVENTION

The present invention involves an improved method for synthesizing cyclic ketene acetals, such as 2-methylene-1,3-dioxepane by dehydrochlorination in the presence of a hydroxide compound in a non-reactive alcohol. This process results in reduced reaction times and reduced number and amount of side reactions and by-products.

The cyclic ketene acetals that are produced according to the process of the present invention are preferably represented by the general formula:

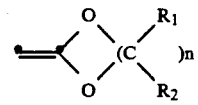

wherein n=2 to 4, and $R_1$ and $R_2$ each independently represent hydrogen or alkyl groups having 1 to 8 carbon atoms, or aryl groups. The preferred cyclic ketene acetals are selected from the group consisting of 2-methylene- 5-dimethyl- 1,3-dioxepane; 2-methylene-5-dimethyl- 1,3 dioxolane; 2-methylene- 5-dimethyl-1,3-dioxane; 4-n-hexyl-2-methylene-1,3-dioxolane; 4-n-octyl2-methylene-1,3-dioxolane; 4-n-decyl-2-methylene-1,3-dioxolane; 2-phenyl-4-methylene-1,3-dioxolane; cis and trans 4,7-dimethyl 2-methylene 1,3-dioxepane; 5,6-benzo 2-methylene 1,3-dioxepane; 2-methylene 4-phenyl 1,3-dioxolane and 2-methylene 1,3-dioxepane with 2-methylene 1,3-dioxepane being most preferred. The preferred halogenated cyclic ketene acetals used to prepare the cyclic ketene acetals are the corresponding chloromethyl compounds such as 2-chloromethyl 1,3-dioxepane.

The halogenated cyclic ketene acetal is preferably prepared by the reaction of the halo acetaldehyde dialkyl acetal with a diol having from 2 to 4 carbon atoms. The preferred halogenated cyclic ketene acetal is 2-chloromethyl 1,3-dioxepane prepared from the reaction of chloroacetaldehyde dimethyl acetal with 1,4-butanediol in the presence of an acid catalyst.

The acid catalyst used in the preparation of the halogenated cyclic ketene acetal can include any acidic compound such as hydrochloric acid, sulfuric acid, para toluene sulphonic acid. The acid is preferably in an acidic ion exchange resin. Examples of suitable acidic ion exchange resins include AMBERLYST 15 and DOWEX 50 produced by Rohm & Haas and Dow Chemical respectively and available from Aldrich Chemicals. The preferred catalyst is an ion exchange resin in fine powder form having a particle size between about 50 and 100 dry mesh.

To produce the cyclic ketene acetal the halogenated cyclic ketene acetal is preferably added incrementally to the reaction solution of the hydroxide compound in the non reactive alcohol. This incremental addition helps control the reaction conditions such as temperature.

The hydroxide compound used in the preparation of the cyclic ketene acetal is selected from alkali metal hydroxides, alkaline earth metal hydroxides and mixtures thereof with the alkali metal hydroxides being more preferred. The most preferred hydroxide compound is selected from potassium hydroxide or sodium hydroxide with potassium hydroxide being most preferred.

The concentration of the hydroxide compound in the non reactive alcohol is between about 20 and 80 weight percent based on a total of the hydroxide compound and alcohol. Much less than 20 weight percent will result in very slow reaction rates and concentrations over 80 weight percent result in a thick slurry hindering proper mixing. The amount of the hydroxide compound in the non reactive alcohol is preferably between about 45 and 65 weight percent with between about 50 and 60 weight percent being most preferred.

The molar ratio of the hydroxide in the hydroxide compound to the halogenated cyclic ketene acetal is at least 1:1 so that all halogenated cyclic ketene acetal is reacted. More hydroxide increases the reaction rate. However, the molar ratio of hydroxide to halogenated cyclic ketene acetal should not be much greater than about 6:1 since it would take a long time to separate the inorganic phase at the end of the reaction. This molar ratio is preferably between about 1.1:1 and 6:1, more preferably between about 2:1 and 5:1 with between about 4:1 and 5:1 being most preferred.

The temperature of the reaction is preferably between about 100° and 130° C. It is preferred that the reaction temperature not be much below 100° C. since the reaction rate is much slower due to poorer solubility of the hydroxide compound in the alcohol at the lower temperature. However, a reaction temperature of much over 130 commences to produce undesirable side reactions resulting in low selectivity. The reaction temperature is preferably between about 115° and 125° C. with between about 120° and 125° C. being most preferred.

The non reactive alcohol is non reactive towards the cyclic ketene acetal. This non reactive alcohol is capable of dissolving the hydroxide compound at the elevated temperature and is preferably selected from 2-butanol, n butanol, t butyl alcohol, and isopropyl alcohol with 2-butanol being the most preferred non reactive alcohol.

The synthesis of the preferred cyclic ketene acetal, 2 methylene 1,3 dioxepane is illustrated by the reaction below.

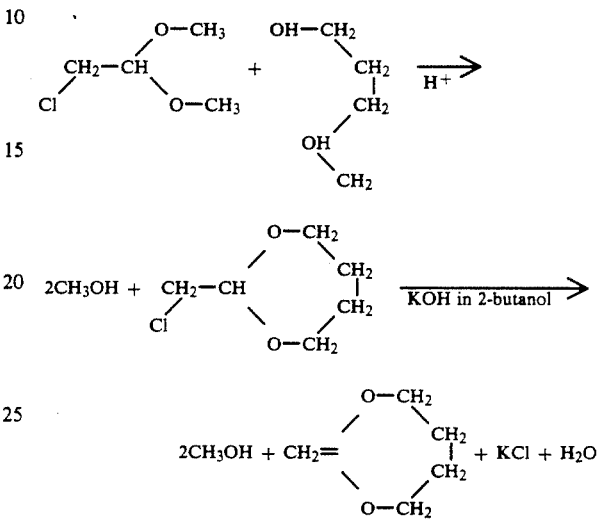

Once the cyclic ketene acetal is prepared it is preferred that the product be purified by removing the organic phase from the inorganic phase and fractionally distilling the organic phase under reduced pressure or inert atmosphere in the presence of an amine. This preferred purification process is more particularly disclosed in the application entitled "Purification of Cyclic Ketene Acetals", by Suabhagya C. Mathur and Jeffrey J. Vanderbilt Ser. No. 07/654,993 Feb. 14, 1991 filed, the disclosure of which is incorporated herein by reference. This purification process more preferably entails separating the organic phrase from the crude mixture with toluene, 1-hexadecene, and triethyl amine. The organic phase is then distilled under partial vacuum resulting in the isolation of the pure cyclic ketene acetal such as pure 2-methylene-1,3-dioxepane without the decomposition or polymerization of the compound.

The following examples are set forth to illustrate the present invention but are not intended to limit the reasonable scope thereof.

EXAMPLES

Example 1-Preparation of 2-chloromethyl-1,3-dioxepane 500 gms of chloroacetaldehyde dimethyl acetal (Aldrich catalog no C1940-6), 360 gms of 1,4-butanediol (Aldrich catalog no. 88,480 7) and 10 gms of Dowex 50 resin (Aldrich catalog No. 21,749 2) were placed in a 1000 ml, 3 neck round bottom flask equipped with a thermometer, a mechanical stirrer, a 8 inch Pen State column, and a distillation head. The mixture was heated to 115° C. under nitrogen blanket and methanol was removed continuously and the amount collected was measured by weigh up. The reaction was monitored by analyzing samples taken from the distillate in a Gas Chromatograph with a dimethyl silicon column in the temperature range of 50° C. to 250° C. The reaction was stopped when the stoichiometric amount of methanol was collected. The crude reaction mixture was filtered to remove the ion exchange resin. The product 2-chloromethyl-1,3-dioxepane was isolated from the crude mixture by fractional distillation in an Oldershaw column under partial vacuum. The fraction boiling at 105° C. at 55 mm of Hg was collected. The structure was confirmed by elemental analysis and proton NMR. Elemental analysis: C-47.2 percent (48 percent calculated), H=7.58 percent (7.33 percent calculated), O=22.64 percent (21.34 percent calculated), Cl=22.57 percent (23.3 percent calculated). Proton NMR:1.71-1.34 ppm multiplet (—OCH$_2$CH$_2$CH$_2$CH$_2$O), 3.46-3.48 ppm doublet (—CH$_2$Cl), 3.66-2.96 ppm 2 sets of triplets OCH$_2$—; 2 sets, 4 protons), 4.83-4.87 ppm triplet (ClCH$_2$CH(O)$_2$).

Example 2—Preparation of 2-methylene-1,3-dioxepane Using Potassium Hydroxide in 2-Butanol 62.5 grams of KOH and 47 gms of 2 butanol were added to a 4 neck 1 liter round bottom flask equipped with a thermometer, a reflux condenser, a pressure relief addition funnel, and a mechanical stirrer. The mixture was heated to 125° C. until all the KOH pellets were dissolved. 37.5 grams of 2-chloromethyl 1,3-dioxepane synthesized using the method described in Example 1 was added drop wise using the addition funnel. After complete addition, the reaction was allowed to occur for 2 hours. Heat was cut off and 100 gms of distilled water and 50 gms of toluene were added to the reaction mixture. The organic phase was separated in a separatory funnel. A gas chromatograph on a sample taken from the reaction mixture indicated complete conversion of 2-chloromethyl-1,3-dioxepane and a 72% crude yield for 2-methylene-1,3-dioxepane was observed.

Example 3

Example 2 was repeated with 270 gms of KOH, 180 gms of 2-butanol and 150 gms of 2-chloromethyl-1,3-dioxepane. The organic phase was taken up in 207 gms of toluene and the inorganic phase was taken in 400 gms of distilled water. At the end of the reaction, 62.9 percent crude yield was observed.

Example 4—Recovery of 2-methylene-1,3-dioxepane from the crude reaction mixture 619 gms of the organic phase collected from examples 2 and 3 Were mixed with 100 gms of 1-hexadecene and 56 gms of Triethyl amine. The mixture was subjected to fractional distillation in an Oldershaw column under partial vacuum. The fraction boiling at 78° C. at 63 mm was collected. The overall yield was 72 percent. 47 percent of the fractions were 99 +percent pure and the remaining portion contained a trace of 2-butanol. The structure of the product was confirmed from proton and C-13 NMR.

Example 5—Comparative Example synthesis of 2-methylene-1,3-dioxepane using KOH in 1-hexadecene 15 gms of 2-chloromethyl 1,3-dioxepane, 60 gms of KOH pellets, 40 mL of 1-hexadecene and 5 gms of Benzyl tributyl ammonium chloride were added into a 300 mL 3 neck round bottom flask equipped with a mechanical stirrer, a thermometer, and a reflux condenser. The mixture was kept at ambient temperature for 20 hours and no reaction occurred. The mixture was then heated to 120° C. Samples for GC were withdrawn at regular intervals to monitor the reaction. Formation of several compounds were indicated but there was no indication of the formation of the desired product. The reaction was continued for 24 hours after adding an additional 30 gms of KOH and 5 gms of Benzyl tributyl ammonium chloride. The desired product did not form.

Example 6—Comparative example synthesis of 2-methylene-1,3-dioxepane using aqueous solution of KOH, 1-hexadecene, and Benzyl tributyl ammonium chloride as phase transfer catalyst 15 gms of 2-chloromethyl 1,3-dioxepane, aqueous KOH (60 gms of KOH dissolved in 40 gms of distilled water), 20 mL of 1-hexadecene and 5 gms of Benzyl tributyl ammonium chloride were added to a 300 mL, 3 neck round bottom flask equipped with a mechanical stirrer, a reflux condenser, and a thermometer. The mixture was heated to 120° C. Samples from the organic phase were withdrawn for GC at regular intervals. Only a trace amount of the product, 2-methylene 1,3-dioxepane, formed while several byproducts formed. The reaction was discontinued after 6 hours.

Example 7—Comparative Example Synthesis of 2-methylene-1,3-dioxepane using tetrabutyl ammonium chloride as the phase transfer catalyst 30 gms of KOH and 100 mL of 1-hexadecene were added to a 300 mL 3 neck round bottom flask equipped with a mechanical stirrer, a thermometer and a reflux condenser. The mixture was heated to b 115° C. and then an additional 90 gms of KOH was added over a period of 90 minutes. The purpose was to get the KOH pellets in solution. 7.5 gms of 2-chloromethyl-1,3-dioxepane was then added to the reaction mixture. The mixture turned brown. A sample was withdrawn for GC but no peak associated with the desired product was detected. 0.28 gms of tetrabutyl ammonium chloride was then added to the reaction mixture and the mixture was heated to 140° C. for 20 hours. Only a trace amount of product formation as indicated by a small peak in GC was detected. The reaction had to be discontinued due to formation of a thick slurry which could not be stirred easily.

Example 8—Comparative example synthesis of 2-methylene-1,3-dioxepane using KOH solution in ethanol 60 gms of KOH pellets were added to 300 mL 3 neck round bottom flask. 40 gms of ethanol was then added. The mixture was heated to 100° C. to obtain reflux conditions. 30.64 gms of 2-chloromethyl-1,3-dioxepane was then added to the mixture. A vigorous reaction occurred and the reaction mixture became a thick slurry very rapidly. The heating was discontinued after 90 minutes. The organic phase was taken up in toluene and the inorganic phase was dissolved in distilled water. GC indicated the peak corresponding to the desired product along with formation of two other major byproducts. 2-methylene-1,3-dioxepane was found to react with ethanol.

Example 9—Comparative example synthesis of 2-methylene-1,3-dioxepane using KOH and t-butyl alcohol Example 8 was repeated using t butanol instead of ethanol. Reflux conditions were obtained at 85° C. The reaction mixture turned brown when 2-chloromethyl-1,3-dioxepane was added. The reaction started to occur at 95° C. After 8 hours, 90 percent conversion occurred.

Two peaks associated with byproducts were seen in GC along with the peak for 2-methylene-1,3-dioxepane. The crude yield was 56 percent, indicating low selectivity towards the desired product.

Example 10—Comparative example synthesis of 2-methylene-1,3-dioxepane using KOH and isopropyl alcohol Example 9 was repeated using isopropyl alcohol instead of t butanol. The formation of 2-methylene-1,3-dioxepane occurred along with 2 major byproducts as observed in the case of Example 9, indicating low selectivity.

The invention has been described in detail with particular reference to the preferred embodiments thereof, however, it should be understood that variations and modifications can be made without departing from the reasonable scope thereof.

I claim:

1. A process for producing cyclic ketene acetals comprising reacting at an elevated temperature a halogenated cyclic ketene acetal with a hydroxide compound selected from alkali metal hydroxides, alkaline earth metal hydroxides and mixtures thereof in a non-reactive alcohol capable of dissolving the hydroxide compound at the elevated temperature, the concentration of the hydroxide compound at the elevated temperature, the concentration of the hydroxide compound in the alcohol solution is between about 20 nd about 80 weight percent based on the total of hydroxide compound and alcohol, thereby producing a cyclic ketane acetal wherein the elevated temperature is sufficient for an adequate reaction rate but not so high as to result in low selectivity.

2. The process according to claim 1 wherein said cyclic ketene acetal is represented by the general formula

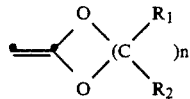

wherein n=2 to 4, and $R_1$ and $R_2$ each independently represent hydrogen, alkyl groups having 1 to 8 carbon atoms, or aryl groups.

3. The process according to claim 2 wherein said cyclic ketene acetal is selected from the group consisting of 2-methylene-5-dimethyl-1,3-dioxepane; 2-methylene-5-dimethyl-1,3-dioxolane; 2-methylene-5-dimethyl-1,3-dioxane; 4-n-hexyl-2-methylene-1,3-dioxolane; 4-n-octyl-2-methylene-1,3-dioxolane; 4-n-decyl-2-methylene-1,3-dioxolane; 2-phenyl-4-methylene-1,3-dioxolane; cis-and trans-4,7-dimethyl-2-methylene-1,3-dioxepane; 5,6-benzo-2-methylene-1,3-dioxepane; 2-methylene-4-phenyl-1,3-dioxolane and 2-methylene-1,3-dioxepane.

4. The process according to claim 3 wherein said cyclic ketene acetal is 2-methylene-1,3-dioxepane.

5. The process according to claim 4 wherein said 2-methylene 1,3-dioxepane is prepared by dehydrochlorination from 2-chloromethyl-1,3-dioxepane.

6. The process according to claim 5 wherein said 2-chloromethyl-1,3-dioxepane is prepared by acetal exchange reaction of chloroacetaldehyde dimethyl acetal with 1,4-butanediol in the presence of an acid catalyst.

7. The process according to claim 1 wherein said hydroxide compound is an alkali metal hydroxide and said non reactive alcohol is selected from 2-butanol, n butanol, t butyl alcohol, and isopropyl alcohol and wherein the concentration of alkali metal hydroxide in alcohol is between about 45 and about 65 weight percent.

8. The process according to claim 7 wherein the alkali metal hydroxide is potassium hydroxide and said non reactive alcohol is 2-butanol.

9. The process according to claim 1 wherein the halogenated cyclic ketene acetal is added incrementally into the solution of the hydroxide compound in the non reactive alcohol and the final molar ratio of the hydroxide in the hydroxide compound to halogenated cyclic ketene acetal is between about 1.1:1 and about 6:1.

10. The process according to claim 1 wherein the elevated temperature is between about 100° C. and 130° C.

11. A process for producing 2-methylene 1,3-dioxepane comprising reacting at an elevated temperature 2-chloromethyl-1,3-dioxepane with a hydroxy compound selected from alkali metal hydroxides, alkaline earth metal hydroxides and mixtures thereof in 2-butanol wherein the concentration of hydroxide compound in 2 -butanol is between about 20 and about 80 weight percent based on the total of hydroxide compound in 2-butanol.

12. The process according to claim 11 wherein the concentration of hydroxide compound in 2-butanol is between about 50 and about 60 weight percent, the molar ratio of hydroxide in the hydroxide compound to 2-chloromethyl-1,3-dioxepane is between about 1:1 to about 6:1, and the reaction is conducted at a temperature between about 100° C. and about 130° C.

* * * * *

UNITED STATES PATENT AND TRADEMARK OFFICE
CERTIFICATE OF CORRECTION

PATENT NO.  : 5,144,046
DATED       : Sept. 1, 1992
INVENTOR(S) : Saubhagya C. Mathur It is certified that error appears in the above-identified patent and that said Letters Patent is hereby corrected as shown below:

On title page, item
[76]  Inventor name reads:   Saughagya C. Mathur should read: --Saubhagya C. Mathur--

Signed and Sealed this

Fourteenth Day of September, 1993

Attest:

BRUCE LEHMAN

Attesting Officer        Commissioner of Patents and Trademarks